(12) United States Patent
Ahn et al.

(10) Patent No.: US 11,826,460 B2
(45) Date of Patent: Nov. 28, 2023

(54) STABLE PHARMACEUTICAL COMPOSITION COMPRISING TESTOSTERONE UNDECANOATE

(71) Applicant: Chong Kun Dang Pharmaceutical Corp., Seoul (KR)

(72) Inventors: Byoung Ki Ahn, Yongin-si (KR); So Hyun Park, Yongin-si (KR)

(73) Assignee: Chong Kun Dang Pharmaceutical Corp., Seoul (KR)

( * ) Notice: Subject to any disclaimer, the term of this patent is extended or adjusted under 35 U.S.C. 154(b) by 231 days.

(21) Appl. No.: 17/261,801

(22) PCT Filed: Jun. 27, 2019

(86) PCT No.: PCT/KR2019/007806
§ 371 (c)(1),
(2) Date: Jan. 20, 2021

(87) PCT Pub. No.: WO2020/022659
PCT Pub. Date: Jan. 30, 2020

(65) Prior Publication Data
US 2021/0259958 A1    Aug. 26, 2021

(30) Foreign Application Priority Data
Jul. 23, 2018    (KR) ........................ 10-2018-0085649

(51) Int. Cl.
| A61K 31/568 | (2006.01) |
| A61K 47/02 | (2006.01) |
| A61K 47/14 | (2017.01) |
| A61K 47/44 | (2017.01) |
| A61K 9/00 | (2006.01) |

(52) U.S. Cl.
CPC .......... *A61K 9/0019* (2013.01); *A61K 31/568* (2013.01); *A61K 47/02* (2013.01); *A61K 47/14* (2013.01); *A61K 47/44* (2013.01)

(58) Field of Classification Search
CPC .... A61K 9/0019; A61K 31/568; A61K 47/02; A61K 47/44
USPC ........................................................ 514/178
See application file for complete search history.

(56) References Cited

U.S. PATENT DOCUMENTS

| 7,718,640 B2* | 5/2010 | Hubler ...................... A61P 5/00 |
| | | 514/181 |
| 9,682,148 B2 | 6/2017 | Hojgaard |
| 2013/0303985 A1 | 11/2013 | Wotton et al. |
| 2018/0071311 A1 | 3/2018 | Dudley et al. |
| 2018/0153904 A1 | 6/2018 | Giliyar et al. |

FOREIGN PATENT DOCUMENTS

| EP | 2682111 A1 | 1/2014 | |
| KR | 20050109561 A | 11/2005 | |
| KR | 100882378 B1 | 2/2009 | |
| KR | 20110103961 A | 9/2011 | |
| KR | 20130124414 A | 11/2013 | |
| KR | 20160081975 A | 7/2016 | |
| WO | WO-9512383 A1 * | 5/1995 | ............. A61K 31/56 |
| WO | 2017024027 A1 | 2/2017 | |
| WO | 2017151911 A1 | 9/2017 | |

OTHER PUBLICATIONS

Islam, D., MehediHasan, M., Mohiuddin, T., Hassan, M., Latif, A., & Haque, P. (2018). Analytical Method Validation of Testosterone Undecanoate Soft Gelatin Capsule by RP-HPLC Method. Journal of Developing Drugs, 7, 1-6. (Year: 2018).*

Merck Sharp Dohme (Australia) Pty Limited. (Apr. 2022). Andriol testocaps. News. Retrieved Nov. 22, 2022, from https://www.news-medical.net/drugs/Andriol-Testocaps.aspx (Year: 2022).*

Behre, et al., "Intramuscular Injection of Testosterone Undecanoate for the Treatment of Male Hypogonadism : Phase I Studies", Eur J Endocrinol, 1999, 140(5), p. 414-419.

Zhang, et al., "A Pharmacokinetic Study of Injectable Testosterone Undecanoate in Hypogonadal Men", J. Androl., 1998, 19(6), p. 761-768.

* cited by examiner

*Primary Examiner* — Yevgeny Valenrod
(74) *Attorney, Agent, or Firm* — Servilla Whitney LLC

(57) ABSTRACT

The present invention relates to an injectable composition of testosterone ester for the treatment of testosterone deficiency. Particularly, the present invention relates to a pharmaceutical composition comprising testosterone undecanoate, which is capable of increasing the convenience for use in injection with the low viscosity and injection force, and has improved stability.

6 Claims, No Drawings

STABLE PHARMACEUTICAL COMPOSITION COMPRISING TESTOSTERONE UNDECANOATE

CROSS-REFERENCE TO RELATED APPLICATIONS

This application is the National Stage entry of PCT/KR2019/007806, filed on Jun. 27, 2019, which claims priority to Korean Application Serial No. 10-2018-0085649, filed Jul. 23, 2018, the entire disclosures of which are hereby incorporated by reference herein.

TECHNICAL FIELD

The present invention relates to an injectable composition of testosterone ester for the treatment of testosterone deficiency. Particularly, the present invention relates to a pharmaceutical composition comprising testosterone undecanoate, which improves the convenience for use in injection with low viscosity and injection force, and has improved stability.

BACKGROUND ART

Testosterone is one of main androgen hormones produced in the interstitial cells of testes, and is responsible for normal growth, development, maintenance and secondary sexual characteristics of the male sex organs.

Testosterone deficiency characterized by the low concentration of testosterone in serum and caused by the insufficient secretion of testosterone may lead to diseases in men, one of which is hypogonadism. Symptoms associated with male hypogonadism include erectile dysfunction, decreased sexual desire, fatigue and loss of stamina, depression, degeneration of secondary sexual characteristics, decreased muscle mass, and increased fat mass. Male hypogonadism is also a risk factor for osteoporosis, metabolic syndrome, type 2 diabetes, cardiovascular diseases, and the like.

Various testosterone replacement therapies have been performed for the treatment of male hypogonadism. These medicines include testosterone or testosterone derivatives in the form of an intramuscular injection, an implant, an oral tablet of alkylated testosterone (for example, methyltestosterone), a topical gel, or a topical patch.

Testosterone is metabolized in the liver and poorly absorbed. Further, methyl testosterone (approved by the US FDA; no product commercially available in Korea) obtained by alkylating a main ingredient in order to prevent metabolism in the liver is limited in long-term administration due to hepatotoxicity.

Fatty acid esters of testosterone act as prodrugs of testosterone. As a relevant drug, product Nebido® (testosterone undecanoate), Delatestryl® (testosterone enanthate), and Depo® (testosterone cypionate) have been developed. Testosterone enanthate and testosterone cypionate have been frequently used as an injectable drug.

A testosterone supplementation therapy includes a testosterone external preparation. However, patches often cause skin side effects such as itching or rash on the skin adhesive surface. An external solution needs to be applied in a predetermined amount daily while medicinal ingredients may be transmitted to other people in contact with the people, so that care needs to be taken.

Recently, the use of testosterone esters having longer aliphatic chains and higher hydrophobicity, for example, testosterone undecanoate represented by Formula 1 below is of great interest in terms of longer injection intervals.

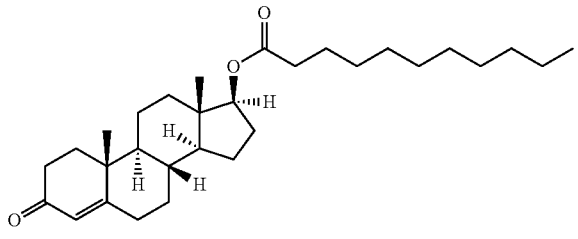

[Formula 1]

A scientific reference discloses that a composition comprising 250 mg of testosterone undecanoate in 2 ml of tea seed oil is prepared, and testosterone undecanoate is injected at a dose of 500 mg or 1,000 mg (Zhang et al., A Pharmacokinetic Study of Injectable Testosterone Undecanoate in Hypogonadal Men: J. Androl., 1998, 19(6), p. 761-768).

Another scientific reference discloses a testosterone undecanoate formulation for testosterone replacement therapy, for example, a composition comprising testosterone undecanoate in tea seed oil (125 mg/ml), and a composition comprising testosterone undecanoate in castor oil (250 mg/ml) (Behre et al., Intramuscular Injection of Testosterone Undecanoate for The Treatment of Male Hypogonadism: Phase I Studies, Eur J Endocrinol, 1999, 140(5), p. 414-419).

U.S. Pat. No. 7,718,640 and Korean Patent No. 0882378 relate to a composition comprising testosterone undecanoate and castor oil. Specifically, an injectable composition comprising testosterone esters which is used for testosterone replacement therapy and applicable for a long period of time is disclosed.

However, the castor oil is inconvenient for use in injection due to the high viscosity and injection force, and has low stability.

Thus, the present inventors performed various experiments to provide an injectable composition which is convenient for use in injection and is stable during long-term storage and transportation to provide a testosterone replacement therapy including testosterone undecanoate, thereby arriving at the present invention.

DISCLOSURE OF INVENTION

Technical Problem

The present invention aims to provide an injectable composition comprising testosterone undecanoate, the injectable composition being a pharmaceutical composition which is convenient for use in injection and is stable during long-term storage and transportation.

Specifically, the present invention aims to provide a pharmaceutical composition comprising testosterone undecanoate which has the increased convenience for use in injection by having low viscosity and injection force, as well as improved stability during long-term storage and transportation.

Solution to Problem

The present invention relates to an injectable composition for sustained release, comprising testosterone undecanoate, and sesame oil or safflower oil.

In the present invention, the term "sustained release" means that testosterone undecanoate as an active ingredient is slowly released over a long period of time. With one administration of the composition, testosterone in blood may be kept constant within a normal concentration range for a long period of time, so that the administration frequency may be reduced and patients' compliance may be increased.

Testosterone undecanoate of the present invention has a structure of Formula 1 as follows:

[Formula 1]

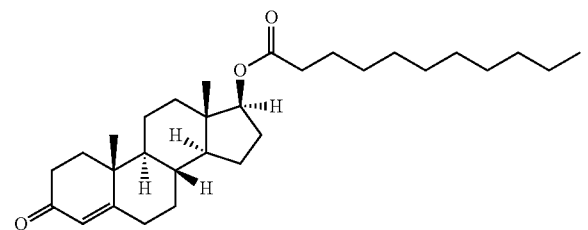

The sesame oil of the present invention is also referred to as sesame seed oil, which means oil obtained from sesame seed, and includes oil refined by compression.

The safflower oil of the present invention is also referred to as *Carthamus tinctorius* oil, which means oil obtained from safflower (*Carthamus tinctorius*) seeds, and includes oil refined by compression.

The present invention relates to a pharmaceutical composition comprising testosterone undecanoate, oil, and a solvent. The solvent is not limited but, preferably, benzyl benzoate. Benzyl benzoate serves to reduce the viscosity and injection force.

The viscosity of the composition of the present invention may be 300 mPas or less, preferably 200 mPas or less, and more preferably 10 to 110 mPas at 4 to 30° C. when measured by the USP rotational rheometer methods. The lower the viscosity of the composition of the present invention is, the lower the injection force of the injection is, so that the convenience in injection may be increased.

When an injection force is measured at an injection rate of 12 mm/min using a 5-mL syringe of which inner diameter is 0.47 inch and which is equipped with a 27G or 29G injection needle having a length of 0.5 inch, the injection force of the composition of the present invention may be 15 N or less when using the 27G injection needle and 40 N or less when using the 29G injection needle.

In the composition of the present invention, a weight ratio of testosterone undecanoate to benzyl benzoate may be 1:0.5 to 1:5, preferably 1:1 to 1:3.

In the composition of the present invention, a weight ratio of testosterone undecanoate to the oil may be 1:0.5 to 1:5, preferably 1:1 to 1:3.

The composition of the present invention may contain 50% or more of an active ingredient when stored during 12 hours under an acidic condition of a 0.15 M to 0.25 M hydrochloric acid solution, preferably under an acidic condition of a 0.16 M hydrochloric acid solution.

The composition of the present invention may be formulated as parenteral administration, for example, as an injectable formulation, and preferably as an intramuscular injectable formulation.

The composition of the present invention is administered preferably every 4 to 16 weeks, more preferably every 10 to 14 weeks.

The composition of the present invention may be administered for the prevention or treatment of hypogonadism.

Advantageous Effects of Invention

The pharmaceutical composition comprising testosterone undecanoate of the present invention may increase the convenience for use in injection with the low viscosity and injection force, and has improved stability under all the acidic, basic, oxidative, and thermal conditions. Therefore, the composition of the present invention may be provided as an improved injectable formulation for the treatment of a patient with testosterone deficiency.

MODE FOR THE INVENTION

Hereinafter, the present invention will be described in more detail through Examples.

However, the Examples are provided merely for helping in understanding the present invention, and the scope of the present invention is not limited by the following Examples.

EXAMPLES

Preparation of Compositions of Examples 1 to 9

According to the composition in Table 1, testosterone undecanoate (hereinafter, referred to as 'TU'), castor oil, sesame oil, safflower oil, or benzyl benzoate (hereinafter, referred to as 'BB') were added and stirred at room temperature for 0.5 to 24 hours to prepare the compositions of Examples 1 to 9.

TABLE 1

| Example | Testosterone undecanoate | Castor oil | Sesame oil | Safflower oil | (Unit: mg) Benzyl benzoate |
|---|---|---|---|---|---|
| 1 | — | 800 | — | — | — |
| 2 | — | — | 800 | — | — |
| 3 | — | — | — | 800 | — |
| 4 | 100 | 1,900 | — | — | — |
| 5 | 100 | — | 1,900 | — | — |
| 6 | 100 | — | — | 1,900 | — |
| 7 | 100 | 120 | — | — | 200 |
| 8 | 100 | — | 120 | — | 200 |
| 9 | 100 | — | — | 120 | 200 |

Test Example 1

Viscosity Measurement

The viscosities of the compositions of Examples 1 to 9 were measured by the following method.

1) Viscosity measurement method: USP 42<912> Rotational rheometer methods—Method IV. Parallel plate (or parallel disk) rheometers 2) Diameter of disk of rheometer: 25 mm 3) Distance to the upper disk: 1 mm 4) Shear rate: 1 to 50 (1/s)

5) Temperature: 4, 15, 25, and 30° C.

6) Sample collection volume: 0.65 mL

The viscosity of Examples 1 to 3 comprising oil alone, measured by the above method, is shown in Table 2 below.

TABLE 2

| | (Unit: mPas, Temperature: 4° C.) | |
|---|---|---|
| Comparison in viscosity of oil | | |
| Example 1 (Castor oil) | Example 2 (Sesame oil) | Example 3 (Safflower oil) |
| 3,791 | 154 | 129 |

As shown in Table 2 above, it was confirmed that the viscosity of Example 2 (sesame oil) and Example 3 (safflower oil) exhibited the values of 154 mPas and 129 mPas, respectively, while the viscosity of Example 1 (castor oil) exhibited the value of 3,791 mPas, which was remarkably higher by 20 times or more than those of Examples 2 and 3.

The viscosity of Examples 4 to 6 in which testosterone undecanoate and oil were comprised, measured by the above method, is shown in Table 3 below.

TABLE 3

| | (Unit: mPas, Temperature: 4° C.) | |
|---|---|---|
| Comparison in viscosity of a composition (TU + oil) | | |
| Example 4 (TU + Castor oil) | Example 5 (TU + Sesame oil) | Example 6 (TU + Safflower oil) |
| 3,822 | 220 | 149 |

As shown in Table 3 above, it can be seen that the viscosity of Example 5 (TU+sesame oil) and Example 6 (TU+safflower oil) exhibited the values of 220 mPas and 149 mPas, respectively, which were increased as compared to that of Examples 2 and 3 comprising oil alone.

Further, it was confirmed that the viscosity of Example 4 (TU+castor oil) exhibited the value of 3,822 mPas, which was remarkably higher than those of Examples 5 and 6.

The viscosity of Examples 7 to 9 in which testosterone undecanoate (TU), oil, and benzyl benzoate (BB) were comprised, measured by the above method, are shown in Tables 4 to 6 below.

TABLE 4

| | | | | (Unit: mPas) |
|---|---|---|---|---|
| Example 7 (TU + Castor oil + BB) | | | | |
| Shear rate | Temperature | | | |
| (1/s) | 4° C. | 15° C. | 25° C. | 30° C. |
| 1 | 216 | 106 | 64 | 48 |
| 2 | 216 | 103 | 63 | 47 |
| 4 | 218 | 102 | 62 | 47 |
| 6 | 218 | 102 | 62 | 48 |
| 11 | 218 | 102 | 61 | 48 |
| 18 | 217 | 101 | 60 | 47 |
| 30 | 217 | 99 | 59 | 46 |
| 50 | 216 | 98 | 58 | 45 |
| Average | 217 | 102 | 61 | 47 |

TABLE 5

| | | | | (Unit: mPas) |
|---|---|---|---|---|
| Example 8 (TU + Sesame oil + BB) | | | | |
| Shear rate | Temperature | | | |
| (1/s) | 4° C. | 15° C. | 25° C. | 30° C. |
| 1 | 97 | 57 | 36 | 30 |
| 2 | 94 | 54 | 36 | 29 |
| 4 | 93 | 53 | 34 | 28 |
| 6 | 93 | 52 | 34 | 28 |
| 11 | 91 | 50 | 33 | 28 |
| 18 | 90 | 49 | 32 | 27 |
| 30 | 89 | 47 | 31 | 25 |
| 50 | 88 | 46 | 30 | 24 |
| Average | 92 | 51 | 33 | 27 |

TABLE 6

| | | | | (Unit: mPas) |
|---|---|---|---|---|
| Example 9 (TU + Safflower oil + BB) | | | | |
| Shear rate | Temperature | | | |
| (1/s) | 4° C. | 15° C. | 25° C. | 30° C. |
| 1 | 85 | 51 | 33 | 29 |
| 2 | 84 | 49 | 33 | 27 |
| 4 | 86 | 48 | 32 | 27 |
| 6 | 86 | 48 | 32 | 27 |
| 11 | 86 | 48 | 32 | 27 |
| 18 | 85 | 47 | 31 | 26 |
| 30 | 84 | 46 | 30 | 25 |
| 50 | 83 | 45 | 29 | 24 |
| Average | 85 | 48 | 32 | 26 |

As shown in Tables 5 and 6 above, it was confirmed that Example 8 (TU+sesame oil+BB) and Example 9 (TU+safflower oil+BB) exhibited the lower viscosity than those of Examples 2 and 3 comprising oil alone or Examples 5 and 6 comprising testosterone undecanoate and oil.

Further, as shown in Table 4 above, it was confirmed that Example 7 (TU+castor oil+BB) exhibited the lower viscosity than that of Example 1 comprising oil alone or Example 4 comprising testosterone undecanoate and oil, but exhibited the high viscosity of 216 mPas or more at 4° C.

It was also confirmed that Examples 8 and 9 maintained a low viscosity even under a wide range of a temperature condition as compared to Example 7, which results in easily applying and using as an injectable formulation.

Test Example 2

Injection Force Measurement

A 5-mL syringe of which inner diameter is 0.47 inch was filled with the compositions of Examples 7 to 9 by 2.5 cm and equipped with a 0.5-inch-long 27G or 29G needle. The syringe was mounted on a MultiTest-dV device manufactured by Mecmesin. The Basic Force Gauge 200 manufactured by Mecmesin was used to measure the injection force (Newton, N) at an interval of 5 to 15 mm while pushing the composition at a rate of 12 mm/min. The results thereof are shown in Table 7 below.

TABLE 7

|  | Example 7 (TU + Castor oil + BB) | Example 8 (TU + Sesame oil + BB) | (Unit: N) Example 9 (TU + Safflower oil + BB) |
|---|---|---|---|
| 27G injection needle | 20.0 | 10.8 | 10.3 |
| 29G injection needle | 53.7 | 29.6 | 29.6 |

As shown in Table 7 above, Example 8 comprising sesame oil and Example 9 comprising safflower oil exhibited the injection force lower than that of Example 7 comprising castor oil.

Therefore, it can be seen that since the composition comprising sesame oil or safflower oil may be injected with low injection force, it is easily injected using a thin injection needle, and may increase the convenience for use in injection.

Test Example 3

Stability Experiment on Compositions of Examples 4 to 6 Through Forced Degradation Test A stability test was performed on Examples 4 to 6, which were a composition comprising testosterone undecanoate and oil, under an acidic, basic, oxidative, or thermal condition using the following experimental method.
1) 0.1 mL of each of Examples 4 to 6 was put into a 20-mL flask adding 3 mL of methanol, and mixing.
2) 6 mL of each of 0.05 M aqueous hydrochloric acid solution (acidic condition), a 0.05 M aqueous sodium hydroxide solution (basic condition), or a 0.5% aqueous hydrogen peroxide solution (oxidative condition) was put into the solution obtained in step 1), mixed, and stored at room temperature for 12 hours.
3) 6 mL of a 0.5% aqueous hydrogen peroxide solution was put into the solution obtained in step 1), and stored at 80° C. for 30 minutes, and then at room temperature for 12 hours (oxidative and thermal conditions).
4) Each of the solutions obtained in steps 2) and 3) was taken, followed by analyzing the content of testosterone undecanoate using HPLC.

The HPLC experimental conditions were as follows.
Detector: UV-VIS spectrophotometer (measurement wavelength: 240 nm)
Column: Kromasil C-18 (4.6 mm×250 mm, 5 um)
Flow rate: 1.5 mL/min
Injection volume: 20 uL
Mobile phase: acetonitrile/distilled water (95/5, v/v)
The analysis results are shown in Table 8 below.

TABLE 8

|  | Example 4 | | Example 5 | | Example 6 | |
|---|---|---|---|---|---|---|
|  | Initial | 12 hours later | Initial | 12 hours later | Initial | 12 hours later |
| Acidic condition | 100% | 33% | 100% | 61% | 100% | 59% |
| Basic condition | 100% | 50% | 100% | 54% | 100% | 49% |
| Oxidative condition | 100% | 41% | 100% | 63% | 100% | 55% |
| Oxidative and thermal conditions | 100% | 41% | 100% | 58% | 100% | 54% |

As shown in Table 8 above, it was confirmed under the acidic condition that Example 5 (TU+sesame oil) and Example 6 (TU+safflower oil) contained 61% and 59% of testosterone undecanoate, respectively, while Example 4 (TU+castor oil) contained 33% of testosterone undecanoate. As such, it can be seen that testosterone undecanoate in Example 4 comprising castor oil was very unstable under the acidic condition as compared to that of Example 5 or 6 comprising sesame oil or safflower oil.

It was confirmed under the oxidative condition and oxidative/thermal conditions that Example 5 (TU+sesame oil) and Example 6 (TU+safflower oil) contained 50% or more of testosterone undecanoate, while Example 4 (TU+castor oil) contained 41% of testosterone undecanoate. Accordingly, it can be seen that testosterone undecanoate in Example 4 comprising castor oil was unstable under the oxidative condition and oxidative/thermal conditions as compared to that of Example 5 or 6 comprising sesame oil or safflower oil.

In sum, it can be seen that Example 5 (TU+sesame oil) and Example 6 (TU+safflower oil) were stable under all the acidic, oxidative, and thermal conditions.

Test Example 4

Stability Experiment on Compositions of Examples 7 to 9 Through Forced Degradation Test A stability test was performed on Examples 7 to 9, which were a composition comprising testosterone undecanoate, oil, and benzyl benzoate (solvent), under an acidic, basic, oxidative, or thermal condition using the following experimental method.
1) 0.1 mL of each of Examples 7 to 9 was put into a 20-mL flask adding 3 mL of methanol, and mixing.
2) 6 mL of a 0.25 M aqueous hydrochloric acid solution was put into the solution obtained in step 1), mixed, and then stored at room temperature for 12 hours (acidic condition).
3) 6 mL of a 0.25 M aqueous sodium hydroxide solution was put into the solution obtained in step 1), mixed, and then stored at room temperature for 12 hours (basic condition).
4) 6 mL of a 2.5% aqueous hydrogen peroxide solution was put into the solution obtained in step 1), mixed, and then stored at room temperature for 12 hours (oxidative condition).
5) 6 mL of a 2.5% aqueous hydrogen peroxide solution was put into the solution obtained in step 1) and stored at 80° C. for 30 minutes, and then at room temperature for 12 hours (oxidative and thermal condition).
6) Each of the solutions in 2) to 5) was taken, followed by analyzing the content of testosterone undecanoate using HPLC.

The HPLC experimental conditions were as follows.
Detector: UV-VIS spectrophotometer (measurement wavelength: 240 nm)
Column: Kromasil C-18 (4.6 mm×250 mm, 5 um)
Flow rate: 1.5 mL/min
Injection volume: 20 uL
Mobile phase: acetonitrile/distilled water (95/5, v/v)
The analysis results are shown in Table 9 below.

TABLE 9

|  | Example 7 | | Example 8 | | Example 9 | |
| --- | --- | --- | --- | --- | --- | --- |
|  | Initial | 12 hours later | Initial | 12 hours later | Initial | 12 hours later |
| Acidic condition | 100% | 36% | 100% | 62% | 100% | 69% |
| Basic condition | 100% | 24% | 100% | 35% | 100% | 33% |
| Oxidative condition | 100% | 45% | 100% | 61% | 100% | 66% |
| Oxidative and thermal conditions | 100% | 47% | 100% | 62% | 100% | 59% |

As shown in Table 9 above, it was confirmed under the acidic condition that Example 8 (TU+sesame oil+BB) and Example 9 (TU+safflower oil+BB) contained 62% and 69% of testosterone undecanoate, respectively, while Example 7 (TU+castor oil+BB) contained 36% of testosterone undecanoate. As such, it can be seen that testosterone undecanoate in Example 7 comprising castor oil was very unstable under the acidic condition as compared to that of Example 8 or 9 comprising sesame oil or safflower oil.

It was confirmed under the oxidative condition and oxidative/thermal conditions that Example 8 (TU+sesame oil+BB) and Example 9 (TU+safflower oil+BB) contained 50% or more of testosterone undecanoate while Example 7 (TU+castor oil+BB) contained 45% and 47% of testosterone, respectively. Thus, it can be seen that testosterone undecanoate in Example 7 comprising castor oil was very unstable under the oxidative condition and oxidative/thermal conditions as compared to that of Example 8 or 9 comprising sesame oil or safflower oil.

It was confirmed under the basic condition that 35% and 33% of testosterone undecanoate were detected in Example 8 (TU+sesame oil+BB) and Example 9 (TU+safflower oil+BB), respectively, while in Example 7 (TU+castor oil+BB), 24% of testosterone undecanoate was detected. As such, it can be seen that testosterone undecanoate in Example 7 comprising castor oil was very unstable under the basic condition as compared to that Example 8 or 9 comprising sesame oil or safflower oil.

In sum, it can be seen that Example 8 (TU+sesame oil+BB) and Example 9 (TU+safflower oil+BB) were stable under all the acidic, basic, oxidative, and thermal conditions as compared to Example 7 (TU+castor oil+BB).

The invention claimed is:

1. An injectable composition for sustained release, comprising testosterone undecanoate as an active ingredient, characterized in that
    the injectable composition comprises sesame oil or safflower oil as oil, and benzyl benzoate as a solvent,
    the injectable composition has a weight ratio of testosterone undecanoate to benzyl benzoate of 1:1 to 1:3 and a weight ratio of testosterone undecanoate to the oil of 1:1 to 1:3, and
    the injectable composition has a viscosity of 10 to 110 mPas at 4 to 30° C. when the viscosity is measured by the USP rotational rheometer method.

2. The injectable composition for sustained release according to claim 1, characterized in that when an injection force is measured at an injection rate of 12 mm/min using a 5-mL syringe of which an inner diameter is 0.47 inch and which is equipped with a 27G or 29G injection needle having a length of 0.5 inch, the injection force is 15 N or less when using the 27G injection needle and 40 N or less when using the 29G injection needle.

3. The injectable composition for sustained release according to claim 1, characterized in that the injectable composition is administered every 4 to 16 weeks.

4. The injectable composition for sustained release according to claim 1, characterized in that the injectable composition contains 50% or more of the active ingredient when stored during 12 hours under an acidic condition of a 0.15 M to 0.25 M hydrochloric acid solution.

5. The injectable composition for sustained release according to claim 1, characterized in that the injectable composition is used for the prevention or treatment of hypogonadism.

6. The injectable composition for sustained release according to claim 1, characterized in that the injectable composition is formulated as an intramuscular injectable formulation.

* * * * *